United States Patent [19]

Lemp

[11] Patent Number: 4,718,420
[45] Date of Patent: Jan. 12, 1988

[54] METHOD AND APPARATUS FOR TREPHINING CORNEAL TISSUE IN PREPARATION FOR KERATOPLASTY

[76] Inventor: Michael A. Lemp, 4918 Hillbrook La., Washington, D.C. 20016

[21] Appl. No.: 836,802

[22] Filed: Mar. 6, 1986

[51] Int. Cl.$^4$ .................................................. A61B 17/16
[52] U.S. Cl. .................................... 128/310; 128/305; 269/294
[58] Field of Search ................... 128/305, 305.1, 310, 128/751–755, 303 R; 604/22; 30/301; 83/522; 269/290–294; 408/76,84; 409/220

[56] References Cited

U.S. PATENT DOCUMENTS

| | | | |
|---|---|---|---|
| 3,058,471 | 10/1962 | Shope | 128/305 |
| 3,074,407 | 1/1963 | Moon et al. | 128/310 |
| 3,515,128 | 6/1970 | McEvoy | 128/753 |
| 3,837,345 | 9/1974 | Matar | 128/305 |
| 4,077,411 | 3/1978 | Ward | 128/305 |
| 4,190,050 | 2/1980 | Bailey | 128/305.1 |
| 4,236,519 | 12/1980 | La Russa et al. | 128/305 |
| 4,336,805 | 6/1982 | Smirmaul | 128/310 |
| 4,423,728 | 1/1984 | Lieberman | 128/310 |
| 4,429,696 | 2/1984 | Hanna | 128/310 |

FOREIGN PATENT DOCUMENTS 3409778 10/1985 Fed. Rep. of Germany ...... 128/305

Primary Examiner—C. Fred Rosenbaum
Assistant Examiner—Mario Costantino
Attorney, Agent, or Firm—Larson and Taylor

[57] ABSTRACT

A method and apparatus for trephining corneal tissue is disclosed which reduces post-operative astigmatism in corneal transplant patients. A donor corneal-scleral button is accurately centered onto a concave surface by means of concentric rings and then held in place, preferably by suction. A rotating circular cutting blade is then lowered through the button to cut out a circular section which forms a donor button. An apparatus to carry out the method of the present invention comprises a curved surface for retaining the corneal-scleral button with circular indicia for positioning the button and apertures for applying a suction thereto. An upper part which is movable into and out of the space immediately above the curved surface mounts a motorized cutting device. The rotational speed and the lowering of the cutting device are controllable by the operator.

14 Claims, 5 Drawing Figures

METHOD AND APPARATUS FOR TREPHINING CORNEAL TISSUE IN PREPARATION FOR KERATOPLASTY

FIELD OF INVENTION

The invention relates to a method and apparatus for trephining corneal tissue in preparation for keratoplasty.

BACKGROUND ON THE INVENTION

A common form of corrective eye surgery is keratoplasty, the transplanting of corneal tissue from a donor to a patient with corneal problems. Advances in the field of keratoplasty have considerably increased the rate of success in these operations. However, this success rate usually relates to the attaining of a clear cornea. There remains a problem with these operations in that post-operative astigmatism following the corneal graft occurs in a large number of cases, and this can severely limit the visual acuity of the patient.

Attempts at controlling this astigmatism have largely been limited to the development of different suturing techniques. These techniques have included the use of different sized non-reactive Nylon sutures, the use of continuous running Nylon sutures, sometimes in combination with interrupted corneal sutures, and other methods. Despite all of these attempts at reducing astigmatism, the results have fallen far short of ideal. Recent studies have shown that astigmatism following suture removal has been largely unaffected by these various suturing techniques. The methods used thus far have not been successful in reducing final astigmatism following corneal transplant and suture removal.

Evidence is starting to accumulate which suggests that the major determinants of astigmatism following corneal grafting appear to be the configuration of the donor button, and the configuration of the recipient bed. One advance in the carving of the recipient bed has been the development of the Barron-Hessburg corneal trephine. This trephine employs a vacuum system for holding a recipient cornea in position while a hand-rotated trephine cuts out a circular section containing the cornea. However, as explained below, the Barron-Hessburg trephine is not suitable for the treatment of donor tissue.

When keratoplasty was originally developed, it was necessary to preserve an entire donor eye. However, with the development of improved preservation techniques, the more recent development has been to preserve only the corneal-scleral tissue (referred to hereinafter as the donor corneal-scleral button). The Barron-Hessburg technique, while possibly suitable for trephining a donor button from an entire donor eye, is not at all suitable for trephining a donor button from a donor corneal-scleral button.

The standard technique for trephining a donor button from a donor corneal-scleral button is to use a trephine which is positioned over a Teflon block. The trephine is brought down on the corneal-scleral button and a donor button is punched out onto the Teflon block. It has been observed that donor buttons punched out in this way demonstrate an elliptical rather than a round shape. This elliptical shape is accentuated if the punching trephine is not extremely sharp. When such an elliptical donor button is placed into a round recipient bed, tissue disparities and distortions result which sometimes become apparent only following suture removal.

In order to avoid the astigmatism which results from these disparities, a need exists for a system which will eliminate or minimize these disparities which occur between the donor button and the recipient cornea bed.

SUMMARY OF THE INVENTION

A purpose of the present invention is to overcome the disadvantages of prior techniques by providing a new and improved trephining method and apparatus, suitable especially for use on a donated corneal-scleral button, which provides a substantially circular button which can then be placed into a recipient corneal bed with minimal tissue disparity, thus significantly reducing the incidence of post-operative astigmatism.

This purpose of the present invention is achieved by providing a method and apparatus for the trephining of a donor button which is characterized by centering a corneal-scleral button on a concave Teflon block which has a series of concentric rings, holding the button onto the block by means of a vacuum, and cutting a circular section by lowering a rotating circular trephining blade through the button until full thickness cutting has been achieved.

The apparatus contemplated by the present invention for carrying out the above method comprises a lowerable, preferably disposable, circular cutting blade which rotates while cutting, a base which holds the concave Teflon block with concentric rings, means for applying suction to the corneal-scleral button upon the concave surface, and means to lower the rotating circular blade onto the button which is positioned on the Teflon block. In order to better insure that a precise circular section is cut from the donor button, it is desirable to use an extremely sharp blade, and to commence circular motion onto the blade before it reaches the corneal tissue. The result of this process in an improved circular section of donor cornea (the donor button) which can then be grafted onto a recipient more effectively than possible heretofore, with a lowered possibility of post-transplant astigmatism.

Thus, it is an object of the present invention to provide a new and improved keratoplasty system, utilizing a donor corneal-scleral button, in which post-operative astigmatism is substantially reduced.

It is another object of the present invention to provide a new and improved apparatus for carrying out the improved keratoplasty method of the present invention.

It is still another object of the present invention to provide a keratoplasty method, of the type described, wherein, with the anterior surface of the corneal-scleral button placed against the receiving trephining block, the accuracy of the holding, positioning and cutting actions upon this button are substantially improved, thus resulting in a more perfectly shaped resultant donor button.

It is still another object of the present invention to provide a new and improved apparatus for carrying out the method of the present invention by providing a system which more accurately holds, positions and cuts the donated corneal-scleral button to provide a more perfectly shaped resultant donor button.

It is still another object of the present invention to provide a new and improved apparatus of the type described wherein the apparatus provides a curved surface for receiving the donated corneal-scleral button with vacuum means or the like for holding this button in place and appropriate indicia for positioning this button onto the curved surface, together with an improved trephining structure which will accurately cut the donor button from this corneal-scleral button.

These and other objects of the present invention will become apparent from the detailed description to follow, taken together with the accompanying drawings.

BRIEF DESCRIPTION OF THE DRAWINGS

There follows a detailed description of preferred embodiments of the present invention which are to be read together with the accompanying drawings wherein.

DETAILED DESCRIPTION OF THE PREFERRED EMBODIMENTS

There follows a detailed description of preferred embodiments of the present invention. In this description, like numerals represent like elements throughout the several views.

Figure 1:
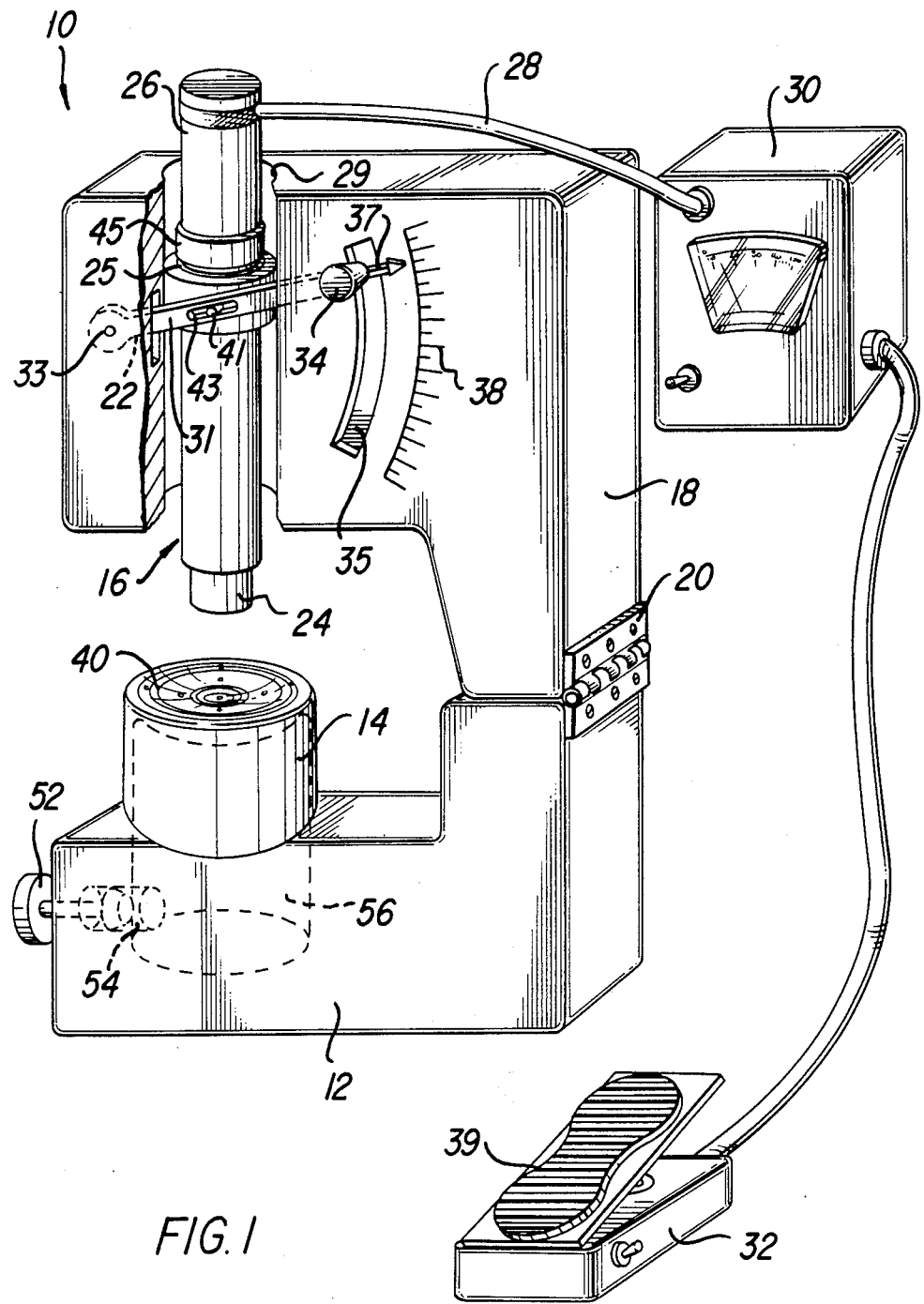
FIG. 1 is a schematic, perspective, partially cutaway view of an apparatus of the present invention, in an operative position.
Figure 2:
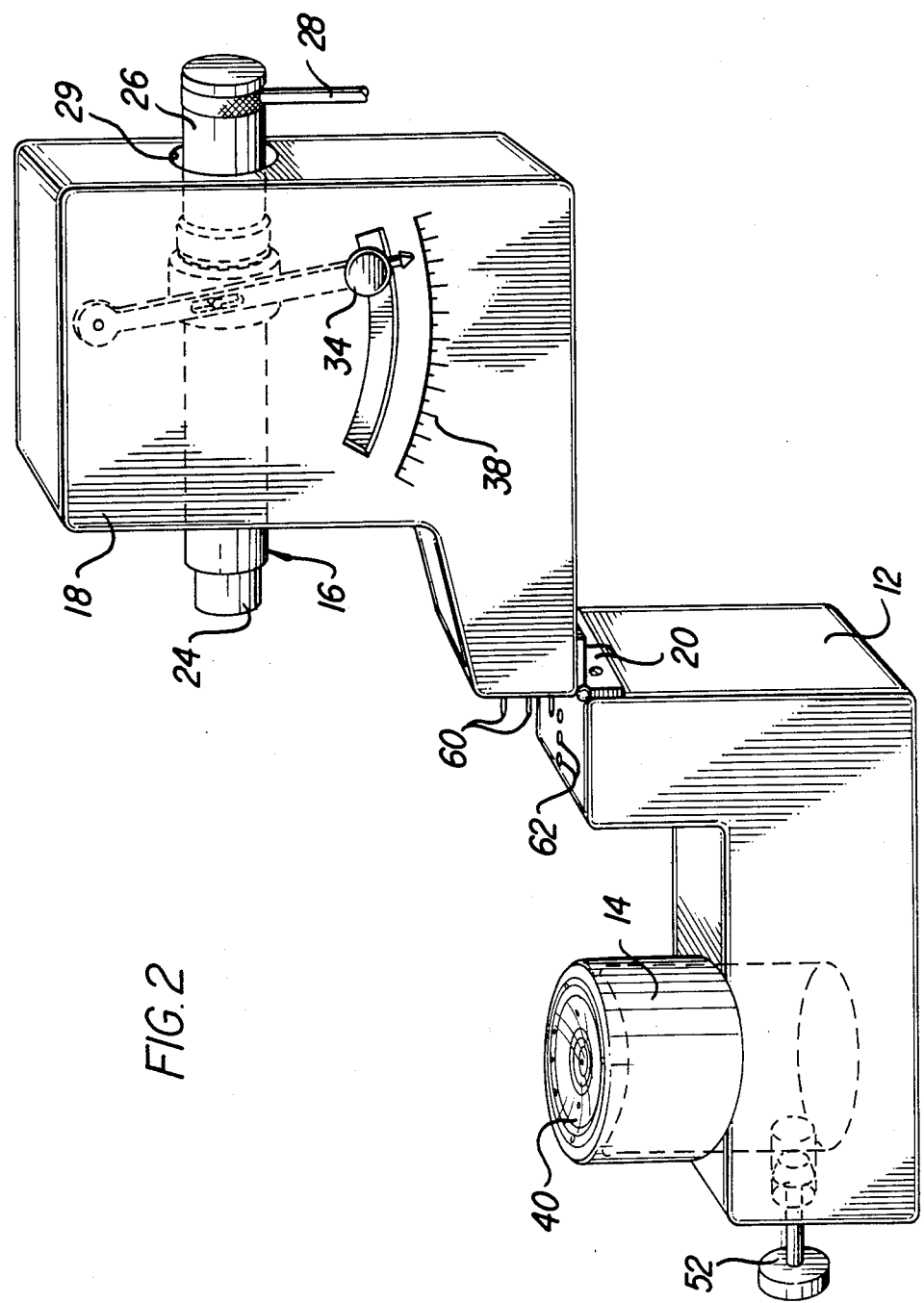
FIG. 2 is a perspective view of a portion of FIG. 1, shown in a different position.

Referring to FIGS. 1 and 2, the trephine 10 comprises a base 12 and an upper part 18. Base 12 includes a concave surface member 14 which is capable of receiving and retaining a corneal-scleral button 50 (see FIGS. 3-5). The trephine 10 also includes cutting device 16 having a blade holding means 26 and a circular trephining blade 24 which are held in position above concave surface member 14 within the vertical through opening 29 of upper part 18. It is necessary to very accurately position the upper part 18 with respect to the base 12, while at the same time allowing the upper part 18 to be removed from its position over the surface member 14 so as to facilitate placement of the corneal-scleral button onto the surface member 14. Although numerous mechanisms may be provided for accomplishing this result, in a preferred embodiment, the upper part 18 is preferably attached to the base by a hinge at point 20 so that the upper part 18 can be swung away from the concave surface member 14 of the base 12, so that a corneal-scleral button can easily be positioned onto the concave surface member 14. Suitable means such as pins 60 and matching holes 62 in the upper part 18 and the base 12 may be used to further assure accurate positioning between the upper part and the base. The apparatus with upper part 18 pivoted back is shown in FIG. 2. The upper part 18 also preferably contains a precision adjustment means 22 for raising and lowering the cutting device 16, with its blade 24, relative to the corneal-scleral button positioned on concave surface member 14.

One type of precision adjustment means for raising and lowering cutting device 16 is shown in FIGS. 1 and 2. The adjustment means 22 comprises a ring 27, with inner friction surface 25, which is connected via its pin 41 and elongated slot 43 to pivot rod 31. The ring 27 fits snugly within opening 29 but is free to slide up and down therein. This pivot rod 31 is attached at one end to a pivot pin 33 fixed in upper part 18, and at the other end turns outward to form handle 34, which extends through slot 35 of upper part 18. The handle 34 can be pulled arcurately down in slot 39 so that ring 27 is lowered, carrying with it cutting device 16, thus lowering circular trephine blade 24 onto the corneal-scleral button so positioned on concave surface member 14. If desired, an arrow 37 can also be attached to pivot rod 31 as it exits slot 35 so that the depth of the blade 24 while it descends can be observed, using suitable depth indicia means 38.

The ring 27 which holds the holding means 26 while it is being lowered may be comprised of metal or plastic. The inner friction surface 25 of ring 27 is preferably rubber, or any other material which can be used to tightly grip the blade holding means 26. Suitable means such as a collar 45 fixed to means 26 can be used to accurately vertically position the means 26 relative to the ring 27.

The cutting device 16, which comprises motorized blade holding means 26 and circular trephine blade 24, is connected to an electrical power source 30 through wires 28. The power source 30, together with the cutting device 16 used in the present invention may be a Barraquer-Mateus keratoplasty drive unit manufactured by Greishaber, or a similar drive unit. It is also possible to provide a foot-switch 32 to operate the power source 30. The foot-switch 32 can be set so that when pedal 35 is depressed the blade 24 begins to rotate at a speed determined by a rheostat device (not shown) on the drive unit.

With these features, an operator can start blade 24 rotating by foot action, adjust the speed of rotation by setting the rheostat, and then lower the rotating blade 24 onto the donor corneal tissue on concave surface member 14 by using adjustment means 22 of the upper part 18.

The trephining blade 24 which fits into blade holding means 26 is a circular, one-piece blade, having a cutting surface which forms a complete circle. This blade 24 is preferably razor sharp all the way aound so as to cut a perfectly circular section from the donor corneal-scleral button, with a minimum of tissue distortion. In this regard, any extremely sharp circular blade may be used, such as those made of tungsten, or stainless steel.

Additionally, it is preferred that the blade 24 is easily attachable to and detachable from the blade holding means 26, and is disposable. In this way, blades for different sized cutting operations can be stored near the trephine, and different sized circular donor buttons can be cut by merely replacing the blade. Circular blades of approximately 7.0, 7.5, 8.0 or 8.5 mm are most often employed for cutting corneal grafts.

Figure 3:
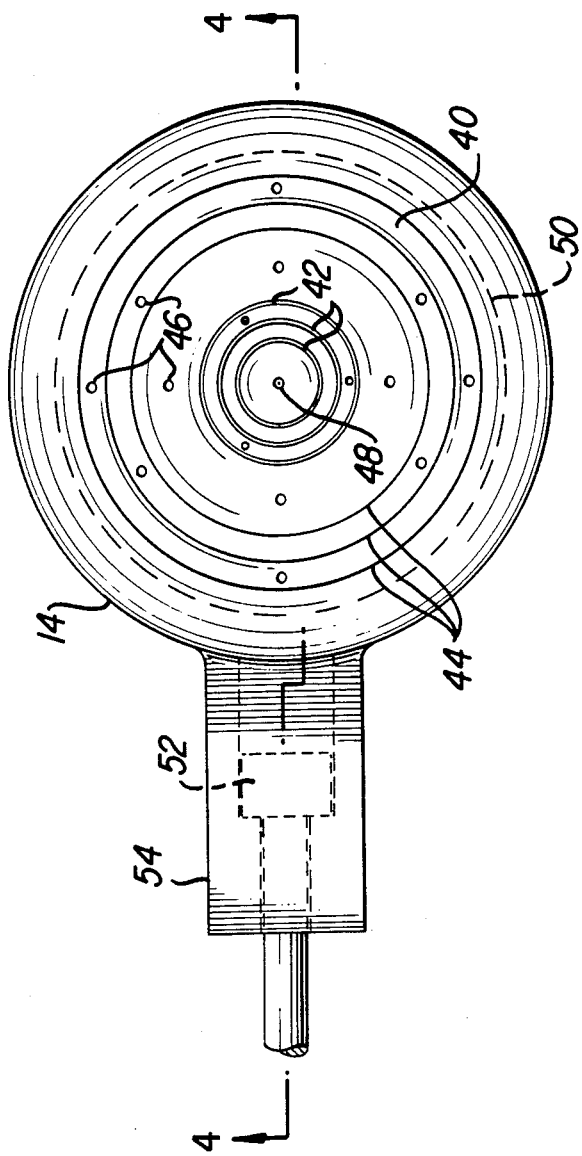
FIG. 3 is an enlarged plan view of a portion of FIG. 1.
Figure 4:
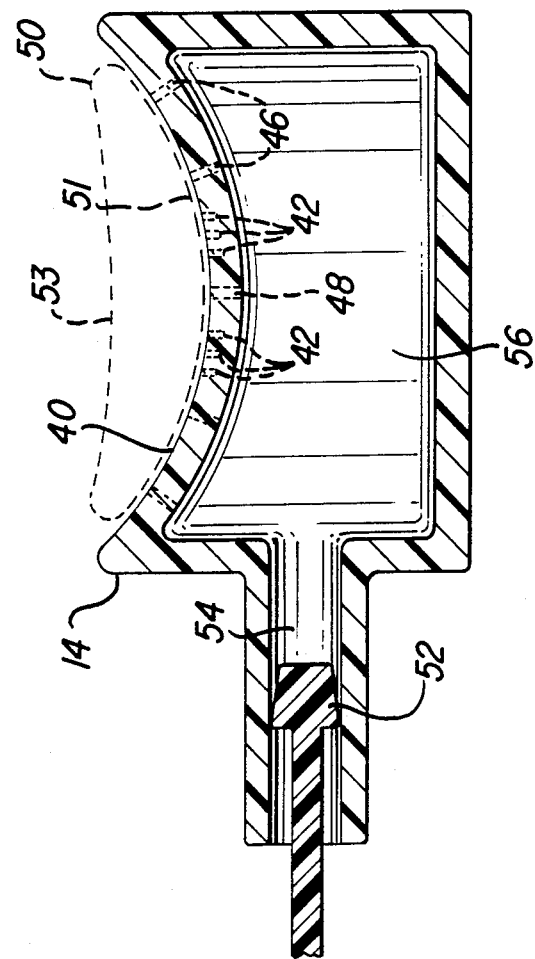
FIG. 4 is a cross-sectional view, taken along line 4—4 of FIG. 3.

The concave surface member 14 which positions and retains the corneal-scleral button so that proper cutting can take place is best shown in FIGS. 3 and 4. The anterior surface of the corneal-scleral button must be placed face down, and it is desirable that the curvature of the curved surface 40 approximate that of an average donor corneal-scleral button. This is to minimize tissue distortion which might otherwise occur during trephining. The ideal concavity which should be used is 42 diopters, the approximate curvature of an average anterior corneal surface.

The concave surface 40 is characterized by a series of concentric circular grooves 42 closer to the center and concentric circular rings 44 further away from the center. The circular grooves are placed at radii which correspond to the blade sizes of the trephine, having diameters of, for example, 7.0, 7.5, 8.0 and/or 8.5 mm so that they sit directly below a correspondingly sized blade 24 of the cutting device 16, to receive the blade after it has cut through a corneal-scleral button. In this way, there is minimal compression of the corneal tissue as the blade cuts through.

The concentric rings 44 act as centering indicia. In order to cut a precise circular section of the corneal-scleral button, the button itself must be perfectly centered on the concave surface 40. The concentric rings 44 act to provide visual confirmation that the transparent circular corneal tissue is perfectly centered on the surface 40. This is possible because the clear corneal tissue is surrounded by opaque scleral matter, and there is a fairly well defined line separating the clear corneal area from the opaque scleral matter. Thus, when the operator places the corneal-scleral button onto the curved surface 40, the button will first be centered, by rough approximation. Then the operator can observe the outermost indicia 44 within but closest to the interface dividing the clear corneal tissue from the opaque scleral tissue and more accurately center the corneal scleral button by moving the button until there is a uniform distance between the outermost visible ring and the interface line dividing the corneal and scleral tissues. Thus, instead of having to visually judge the position of an entire corneal-scleral button with respect to the entire surface 40, the operator can focus his attention on only the minimal distance between the outermost visible indicia 44 and the interface line dividing the corneal and opaque tissues, and simply assure that there is uniformity completely around the entire ring within the said interface line.

After the corneal-scleral button is perfectly centered on surface 40, it is necessary to apply suction to the concave surface in order to hold the button in this position. In the preferred embodiment, this is accomplished through a series of holes 46, including central opening 48, which allow the operator to transmit a suction force to the corneal-scleral button 50. The suction can be provided by a vacuum syringe apparatus, as best seen in FIGS. 3 and 4. In this apparatus, a syringe 52 can be pulled outwards from channel 54 in order to create a vacuum by evacutating air from chamber 56. This vacuum force creates suction through the central openings 48 and the series of holes 46 so that the corneal-scleral button 50 is held tightly on concave surface 40. When held in this manner, the centered button 50 can be efficiently trephined by the cutting device 16.

It is preferred that the base 12 and upper part 18 of the appparatus are made of Teflon, which provides a sturdy and resilient base for the cutting procedure. However, any other suitable material, such as various hard plastics, may also be employed.

As will be apparent to those skilled in the art, there may be numerous modifications and alterations possible from the above described preferred embodiment without departing from the scope of the present invention. For instance, it is not necessary that the upper part be hingedly attached to the base. Alternatively, a cutting apparatus could be suspended over the concave surface 40 member by other means, and then lowered onto the corneal-scleral button as in, for example, a mechanical drill press.

The method of the present invention will now be described, especially in the context of utilizing the above described preferred embodiment of the apparatus of the present invention. First, the surface 40 of the surface member 14 must be made readily accessible to facilitate placement of the corneal-scleral button 50 thereon. Utilizing the above described apparatus, such placement may be simplified by simply pivoting the upper part 18 to the position as shown in FIG. 2, thus fully exposing the surface 40 of the surface member 14. Alternatively, the cutting device 16 can itself be removed from the opening 29 in the upper part 18, thus allowing for easy detachment and reattachment of the disposable blade 24. The cutting device 16 can be reinserted into opening 29 and secured to the adjusting means 22 while the upper part 18 is in the swung out position of FIG. 2. The cutting device 16 can be secured to the adjusting means 22 by inserting blade holding means 26 through ring 27, which is in turn attached to the pivot rod 31 of the adjusting means. When in place, the cutting device 16 is lowered by pulling down on handle 34 at the end of piston rod 31.

Figure 5:
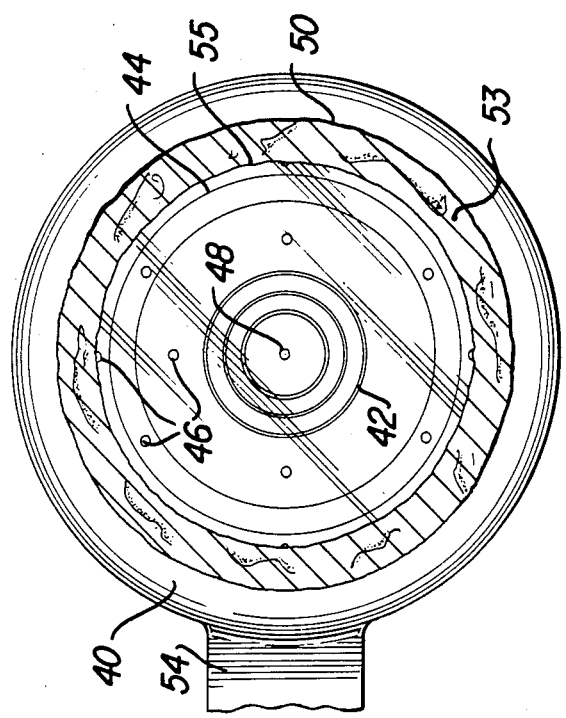
FIG. 5 is a top view, similar to FIG. 3, showing schematically the operation of the present invention.

Precise positioning of the corneal-scleral button 50 is essential to the precise cutting of a perfectly circular donor button for transplant purposes. As shown in FIG. 5, a tissue-preserved corneal-scleral button 50 is placed on concave surface 40 so that its anterior surface is flush against concave surface 40 and its posterior surface 53 faces upwards, towards the cutting appararus. This positioning is essential in minimizing distortion to the corneal graft, as the posterior surface of the cornea is very sensitive to pressure. Cutting from the anterior surface would more heavily impinge upon the posterior surface, and cause great disruption of this sensitive tissue. By placing the button with its posterior surface facing the cutting apparatus, there is less pressure applied to this surface, and thus the damage to this area is minimized when the cutting blade is applied.

The button 50 is placed approximately at the center of concave surface 40. To center the button exactly, the discernable interface 55 between the clear corneal tissue and whitish opaque scleral tissue is maneuvered so that it either coincides with or is slightly outward of one of the concentric rings 44 of the concave surface 40. The corneal-scleral button is then carefully positioned either to coincide with that ring, or as described above, to establish a uniform distance between the outermost visible ring 44 and the interface 55, all the way around. At this point, suction is immediately applied so as to keep button 50 in this centered position for the duration of the trephining procedure.

Using the apparatus described above, suction can immediately be carried out upon centering of the corneal-sleral button 50 by the pulling out of the syringe 52 on the base 12 of the apparatus. The suction created in chamber 56 by pulling the syringe 52 outwards is transmitted through central opening 48 and other holes 46 spread throughout the concave surface 40 to pull the anterior surface 51 of the corneal-scleral button 50 tightly against the concave surface 40.

Once the button 50 is centered, and suction has been applied, the button is ready for cutting. At this point, the upper part 18 can be placed in an upright position, as shown in FIG. 1. The cutting device 16, with a desired blade 24 in place, reinserted into opening 29 in upper part 18, now sits directly above the concave surface member 14 which holds button 50, and the cutting procedure can begin.

Before or during lowering of the cutting device 16, the motorized blade holding means 26 is turned on so that the blade 24 rotates along its circumference before it reaches the posterior surface 53 of the corneal-scleral button. The rotational speed of the blade 24 can be set by adjusting the rheostat before or during the lowering step. While the blade 24 is turning in a circular motion, the cutting apparatus is then lowered onto posterior surface 53 by means of the hand-operated adjusting device 22.

As the sharp rotating blade 24 engages the tissue on the button's posterior surface, it is cutting immediately. This eliminates much of the distortion which resulted from the use of the previously known conventional punch trephine. In the present invention, tissue distortion is reduced substantially. The rotating blade 24 is continually lowered after encountering posterior surface 53, and continues cutting throughout the depth of the corneal tissue. When the blade finishes cutting through the anterior surface 51 of the corneal button, it continues into whichever groove 42 of concave surface 40 matches the diameter of the particular blade used. After full thickness cutting of a circular section through the button is achieved, the blade is then withdrawn by raising the handle 22.

After the cutting blade has been raised, the power is turned off, and the upper part 18 is swung back once more to again allow access to concave surface member 14. At this point, the suction is removed, and the circular donor button is removed from the concave surface 40. The circular section of donor corneal tissue, i.e. the donor button, can now be transferred into the recipient eye. The recipient eye will have had a section cut out of it by a trephine blade equal in size to the one used to cut the donor button. The corneal graft donor button obtained from this process is inserted into the recipient and sutured.

As a result of the above techniques, the disparity in shape between the donor button and the recipient cornea is substantially minimized. The use of these techniques in the trephining of corneal tissue for transplants will thus greatly reduce the incidence of post-operative astigmatism which has resulted from previously known prior art methods of corneal grafting.

Although the invention has been described in considerable detail with respect to preferred embodiments, it will be apparent that the invention is capable of numerous modifications and variations, apparent to those skilled in the art, without departing from the spirit and scope of the invention.

I claim:

1. A method of preparing a corneal tissue for keratoplasty, comprising the steps of:
   placing a corneal-scleral donor button onto a concave surface with its anterior surface against the concave surface and its posterior surface facing away from the concave surface,
   centrally positioning the donor button on the concave surface by visually matching indicia on the concave surface with physical characteristics of the donor button,
   with the donor button centrally positioned, securely adhering the donor button to the concave surface by applying suction to the button through openings in the concave surface,
   and advancing a circular cutting blade toward the donor button, while the donor button is adhered to the concave surface, said advancement being in a direction substantially parallel to and coaxial with the axis of the concave surface, starting the cutting blade into its circular motion before it engages the donor button, continuing the circular motion of the cutting blade as it advances completely through the donor button and past the anterior surface of the donor button and into a circular blade receiving groove formed in the concave surface.

2. A method of preparing a corneal tissue for keratoplasty as claimed in claim 1, wherein the positioning step includes positioning the button on the surface by visually matching at least one centered ring on the surface with the interface between the clear corneal tissue and the opaque scleral tissue of the button.

3. A method of preparing a corneal tissue for keratoplasty as claimed in claim 1, wherein suction is applied to the button from beneath the surface by means of a vacuum syringe slidably positioned in a channel connected to a chamber beneath the surface, said suction applied by pulling said syringe outwardly from said chamber along said channel, and said suction transmitted to the button by means of at least one opening in the concave surface which extends through the surface and into said chamber.

4. An apparatus for preparing a corneal tissue for keratoplasty, comprising:
   a base having a concave surface for supporting a corneal-scleral donor button with the anterior surface of the donor button against the concave surface and the posterior surface of the donor button facing away from the concave surface,
   said concave surface having indicia means for cooperating with physical characteristics of the donor button to assist in visually centering the donor button on the concave surface,
   said base having suction means for adhering a centered donor button to said concave surface by acting on the donor button through the concave surface,
   a cutting means comprising a cutting blade mounted in a blade holding means and movable circularly about an axis coincident with the axis of the concave surface,
   advancing means mounting the cutting blade for advancing movement toward the concave surface in a direction substantially parallel to and coaxial with the axis of the concave surface,
   said concave surface having at least one circular groove formed therein which is aligned with the cutting blade and positioned to receive the cutting blade after it has advanced axially completely through the donor button,
   power means for rotating the cutting blade and means for advancing the cutting blade to and through the donor button and into the circular groove formed in the concave surface, and said power means having means for commencing circular movement of the cutting blade before it reaches the donor button and maintaining said circular movement until the cutting blade has passed axially completely through the donor button and into said aligned circular groove, to therbey cut a finished donor button out of the corneal-scleral donor button.

5. An apparatus for preparing a corneal tissue for keratoplasy as claimed in claim 4, wherein said indicia means comprises at least one ring whose center is the center of the concave surface.

6. An apparatus for preparing a corneal tissue for keratoplasy as claimed in claim 4, wherein said indicia means comprises a series of three concentric rings having diameters of 9, 10, and 11 mm, respectively.

7. An apparatus for preparing a corneal tissue for keratoplasy as claimed in claim 4, wherein said concave surface comprises four of said circular grooves, said grooves being concentric and having diameters of 7.0, 7.5, 8.0 and 8.5 mm, respectively.

8. An apparatus for preparing a corneal tissue for keratoplasy as claimed in claim 4, wherein said suction means comprises a vacuum syringe apparatus, said vacuum syringe apparatus comprising a chamber below and in communication with said concave surface, a channel extending outwardly from said chamber, a syringe slidably retained in said channel, and at least one opening in said concave surface through which a suction force created in said chamber can be transmitted to a button positioned on said surface, said vacuum syringe apparatus having means for pulling said syringe along said channel outwardly from said channel.

9. An apparatus for preparing a corneal tissue for keratoplasy as claimed in claim 4, wherein said circularly movable blade is detachable from the blade holding means.

10. An apparatus for preparing a corneal tissue for keratoplasy as claimed in claim 4, wherein said power means comprises an electrical power source.

11. An apparatus for preparing a corneal tissue for keratoplasty as claimed in claim 4, wherein said cutting means is positioned directly over said concave surface on an upper part extending upwardly from said base, said upper part having means for holding said cutting means above said concave surface, and said advancing means comprising means for lowering said cutting means onto said concave surface.

12. An apparatus for preparing a corneal tissue for keratoplasy as claimed in claim 11, wherein said upper part is hingedly attached to said base so that said upper part can be swung away from said base to allow clear access to said concave surface and allow easy positioning of a corneal-scleral button on said concave surface.

13. An apparatus for preparing a corneal tissue for keratoplasy as claimed in claim 11, wherein said upper part is comprised of Teflon.

14. An apparatus for preparing a corneal tissue for keratoplasy as claimed in claim 4, wherein said base is comprised of Teflon.

* * * * *